US009539270B2

(12) United States Patent
Sallomons et al.

(10) Patent No.: US 9,539,270 B2
(45) Date of Patent: Jan. 10, 2017

(54) METHODS FOR PROVIDING SIALYLATED OLIGOSACCHARIDES

(71) Applicants: Friesland Brands B.V., Amersfoort (NL); Rijksuniversiteit Groningen, Groningen (NL); Darling Ingredients Nederland B.V., Son (NL)

(72) Inventors: Erik Sallomons, Westerbork (NL); Maarten Hotse Wilbrink, Groningen (NL); Peter Sanders, Groningen (NL); Johannis Paulus Kamerling, Groningen (NL); Catherina Anna van Vuure, Helmond (NL); Johannes Adrianus Hage, Arkel (NL)

(73) Assignee: RIJKSUNIVERSITEIT GRONINGEN, Groningen (NL)

( * ) Notice: Subject to any disclaimer, the term of this patent is extended or adjusted under 35 U.S.C. 154(b) by 96 days.

(21) Appl. No.: 14/363,856

(22) PCT Filed: Dec. 6, 2012

(86) PCT No.: PCT/NL2012/050857
§ 371 (c)(1),
(2) Date: Jun. 9, 2014

(87) PCT Pub. No.: WO2013/085384
PCT Pub. Date: Jun. 13, 2013

(65) Prior Publication Data
US 2014/0336140 A1  Nov. 13, 2014

(30) Foreign Application Priority Data
Dec. 7, 2011 (NL) ..................................... 2007931

(51) Int. Cl.
| | | |
|---|---|---|
| C08B 37/00 | (2006.01) | |
| A61K 31/7028 | (2006.01) | |
| A61K 31/702 | (2006.01) | |
| A61K 31/715 | (2006.01) | |
| C12P 19/26 | (2006.01) | |
| C12P 19/28 | (2006.01) | |
| C07H 3/06 | (2006.01) | |
| C12P 19/00 | (2006.01) | |
| C12P 19/04 | (2006.01) | |
| C12P 19/14 | (2006.01) | |

(52) U.S. Cl.
CPC ......... *A61K 31/7028* (2013.01); *A23K 20/163* (2016.05); *A23K 50/10* (2016.05); *A23K 50/30* (2016.05); *A23K 50/60* (2016.05); *A23L 29/30* (2016.08); *A23L 33/21* (2016.08); *A23L 33/40* (2016.08); *A61K 31/702* (2013.01); *A61K 31/715* (2013.01); *C07H 3/06* (2013.01); *C12P 19/00* (2013.01); *C12P 19/04* (2013.01); *C12P 19/14* (2013.01); *C12P 19/26* (2013.01); *C12P 19/28* (2013.01); *A23V 2002/00* (2013.01); *C12Y 302/01018* (2013.01); *Y02P 20/52* (2015.11)

(58) Field of Classification Search
None
See application file for complete search history.

(56) References Cited

U.S. PATENT DOCUMENTS

| | | |
|---|---|---|
| 5,260,280 A | 11/1993 | Isoda et al. |
| 5,514,660 A | 5/1996 | Zopf et al. |
| 5,620,965 A | 4/1997 | Blank |
| 5,753,630 A | 5/1998 | Zopf et al. |
| 5,834,423 A | 11/1998 | Koketsu et al. |
| 5,883,079 A | 3/1999 | Zopf et al. |
| 7,893,041 B2 * | 2/2011 | Morrow ............... A61K 31/702 514/3.1 |
| 9,290,530 B2 * | 3/2016 | Chen ........................ C07H 1/00 |
| 2007/0004656 A1 | 1/2007 | Schmitt et al. |
| 2007/0104843 A1 | 5/2007 | Holst et al. |

FOREIGN PATENT DOCUMENTS

| | | |
|---|---|---|
| EP | 1549151 | 7/2005 |
| WO | 9425615 | 11/1994 |
| WO | 0160346 | 8/2001 |
| WO | 2004032639 | 4/2004 |
| WO | 2004055176 | 7/2004 |
| WO | 2009113861 | 9/2009 |

(Continued)

OTHER PUBLICATIONS

Yu et al., "Chemoenzymatic Synthesis of GD3 Oligosaccharides and Other Disialyl Glycans Containing Natural and Non-natural Sialic Acids" JACS (2009) vol. 131 pp. 18467-18477.*
Mendoza et al., "Synthesis of the O-linked pentasaccharide in glycoproteins of Trypanosoma cruzi and selective sialylation by recombinant trans-sialidase" Carbohydrate Research (2006) vol. 341 pp. 1488-1497.*
Van Halbeek et al, "A 360-MHz $^1$H-NMR Study of Three Oliogosaccharides Isolated From Cow κ-Casien", Biochimica et Biophysica Act, vol. 623, pp. 295-300, 1980.
Hansson et al, "Analysis of sialic acid-containing mucin oligosaccharides from porcine small intestine by high-temperature gas chromatography-mass spectrometry of their dimethylamides", Carbohydrate Research, vol. 221, pp. 179-189, 1991.

(Continued)

*Primary Examiner* — Eric Olson
(74) *Attorney, Agent, or Firm* — Hoffmann & Baron, LLP (57) ABSTRACT

The invention relates to a method for providing analogs of human milk oligosaccharides (HMO), in particular oligosaccharides containing terminal sialic acid. The method comprises the steps of: a) providing a source of non-digestible galactooligosaccharides (GOS) containing at least two terminally bonded β-linked galactose residues; b) providing a sialic acid donor having (α2-3)-sialylated O-glycans; c) contacting said GOS with said sialic acid donor in the presence of an enzyme having trans-sialidase activity in an enzyme reaction mixture; and d) isolating from said enzyme reaction mixture a fraction comprising at least 20 percent by weight of disialylated galactooligosaccharides (di-Sia-GOS) based on the dry matter.

19 Claims, 7 Drawing Sheets

(56) References Cited

FOREIGN PATENT DOCUMENTS

WO        2010116317        10/2010

OTHER PUBLICATIONS

Scudder et al, "Enzymatic Characterization of β-D-Galactoside α2,3-trans-Sialidase from Trypanosoma cruzi*", The Journal of Biological Chemistry, vol. 268, No. 13, Issue of May 5, pp. 9886-9891, 1993.

Idota et al, "Inhibition of Cholera Toxin by Human Milk Fractions and Siolyllactose", Biosci. Biotech. Biochem, vol. 59(3), pp. 417-419, 1995.

Yanahira et al, "Formation of Oligosaccharides from Lactose by Bacillus circulans β-Galactosidase", Biosci. Biotech. Biochem, vol. 59 (6), pp. 1021-1026, 1995.

Simon et al, "Inhibition of Helicobacter pylori binding to gastrointestinal epithelial cells by sialic acid-containing oligosaccharides", Infection and Immunity, vol. 65 (2): 750, 1997.

Fransen et al, "α-DGLCp-(1-1)-β-D-Galp-containing oligosaccharides, novel products from lactose by the action of β-galactosidase", Carbohydrate Research, vol. 314, pp. 101-114, 1998.

Paris et al, "Probing molecular function of trypanosomal sialidases: single point mutations can change substrate specificity and increase hydrolytic activity", Glycobiology, vol. 11, No. 4, pp. 305-311, 2001.

Turnbull et al, "Observations on chemical and enzymatic approaches to α-2,3-sialylated octyl β-lactoside", Tetrahedron, vol. 58, pp. 3207-3216, 2002.

Goulas et al, "Purification of oligosaccharides by nanofiltration", Journal of Membrane Science, vol. 209, pp. 321-335, 2002.

Neubacher et al, "Preparation of sialylated oligosaccharides employing recombinant trans-sialidase from Trypanosoma cruzi", Org. Biomol. Chem, vol. 3, pp. 1551-1556, 2005.

Agusti et al, "The trans-sialidase from Trypanomsoma cruzi efficiently transfers α-(2-3)-linked N-glycolylneuraminic acid to terminal β-galactosyl units", Carbohydrate Research, vol. 342, pp. 2465-2469, 2007.

Asakuma et al, "Sialyl Oligosaccharides of Human Colostrum: Changes in Concentration during the First Three Days of Lactation", Biosci. Biotechnol. Biochem., vol. 71 (6), pp. 1447-1451, 2007.

Coulier et al, "In-Depth Characterization of Prebiotic Galactooligosaccharides by a Combination of Analytical Techniques", Journal of Agricultural and Food Chemistry, vol. 57, pp. 8488-8495, 2009.

Thurl et al, "Variation of human milk oligosaccharides in relation to milk groups and lactational periods", British Journal of Nutrition, pp. 1-11, 2010.

Schauer et al, The Chemistry and Biology of Trypansomal trans-Sialidases: Virulence Factors in Chagas Disease and Sleeping Sickness, ChemBioChem, pp. 1-20, 2011.

* cited by examiner

METHODS FOR PROVIDING SIALYLATED OLIGOSACCHARIDES

This application is the U.S. National Phase of, and Applicants claim priority from, International Patent Application Number PCT/NL2012/050857 filed 6 Dec. 2012, which claims priority from NL2007931 filed 7 Dec. 2011, each of which is incorporated herein by reference.

The invention relates to a method for providing analogs of human milk oligosaccharides (HMO), in particular oligosaccharides containing terminal sialic acid (hereinafter: sialic acid containing oligosaccharides), especially sialylated galactooligosaccharides (Sia-GOS). In addition, the invention relates to the obtainable sialylated oligosaccharides and the use thereof, in especially infant foods and animal feed.

Human milk contains a large quantity and diversity (>100 structures) of oligosaccharides with different physiological functions, including as prebiotic components and antiadhesive components for pathogenic microorganisms. Especially sialic-acid-containing oligosaccharides (SOS) were shown to inhibit adhesion of pathogenic microorganisms, including *E. coli* and *Salmonella* spp. in the small intestine. SOS are abundantly present in human milk (0.6-3.3 g/l) and can reach even higher concentrations in milk of the earliest stage of lactation (colostrum). In cow milk, however, SOS are present only in very small amounts. Therefore, a great discrepancy between human milk and infant formula based on cow milk exists concerning the abundance of SOS.

In the sialylated oligosaccharides of human milk, N-acetylneuraminic acid (Neu5Ac) is attached to a penultimate galactose residue via $\alpha 2$-3 or $\alpha 2$-6 linkages or to an internal N-acetylglucosamine residue via an $\alpha 2$-6 linkage, formed by the action of sialyltransferases. Several pathogenic microorganisms, such as *Vibrio cholerae*, *Escherichia coli*, *Helicobacter pylori*, and influenza viruses A and B, recognize a sialic-acid-containing carbohydrate receptor structure on target cells; sialylated components in human milk may therefore function as soluble receptor analogs to inhibit the attachment of these pathogens to cell surface receptors. It has been proposed that sialic acid is used for the synthesis of infant brain gangliosides and sialylglycoproteins. The fact that human milk is a rich source of sialic acid for infants suggests that the rapid formation of brain gangliosides during first month post partum depends on metabolic utilization of milk sialyl-oligosaccharides and sialylglycoconjugates.

Since, as a rule, the aim is to make infant and baby foods resemble human milk as much as possible, several investigators recognized the need (especially with infant milk formulations) to enrich such foods with sialic-acid-containing oligosaccharides.

The focus has been predominantly on sialyllactoses since these are present at noticeably higher concentrations in human milk compared to other mammalian species. Sialyllactose is known to have anti-adhesive properties for specific pathogenic bacteria. For example, sialyllactose acts to inhibit cholera toxin in vitro (Idota et al., Biosci. Biotech. Biochem. 59: 417-419, 1995) and *Helicobacter pylori* (Simon et al., Infection and Immunity 65: 750-757, 1997).

In light of its anti-adhesive properties, sialyllactose has been used to treat or prevent a number of medical conditions. For example, U.S. Pat. No. 5,260,280 discloses a composition containing sialic-acid-containing oligosaccharides that neutralizes the effects of bacterial enterotoxin. U.S. Pat. No. 5,514,660, U.S. Pat. No. 5,753,630 and U.S. Pat. No. 5,883,079 disclose methods for treating or preventing an ulcer in the stomach or duodenum or inhibiting *Helicobacter pylori* infection, respectively, by administering an effective amount of a sialic-acid-containing oligosaccharide. U.S. Pat. No. 5,620,965 relates to compositions for inhibiting binding of the bacterium *Helicobacter pylori* to stomach or duodenal cells by administering an effective amount of certain oligosaccharides. U.S. Pat. No. 5,834,423 describes sialic acid derivatives that promote the proliferation of bifidobacteria and the use of effective amounts of certain sialylated oligosaccharides as an antidiarrheal agent. The sialylated oligosaccharides comprise 3'-sialyllactose and 6'-sialyllactose (sialic acid=Neu5Ac). WO2001060346 discloses a nutritional composition comprising the prebiotic substances oligofructose and sialyllactose that act synergistically to stimulate the growth of the beneficial bifidobacteria. WO01/60346 discloses nutritional compositions, such as an infant formula, comprising oligofructose and sialyllactose. EP 1549151 describes that the combination of oligofructose, sialyllactose and probiotic bacteria eradicates intestinal infection with pathogenic bacteria, particularly enteropathogenic *E. coli*, and may therefore be used for the prophylaxis of diarrhea due to enteropathogenic *E. coli*. US20070104843 relates to a milk-derived sialyllactose concentrate for the use in foods especially intended for infants, children or elderly persons as well as foods for medical or dietetic purposes and other food applications. It also discloses a process for producing the sialyllactose concentrate comprising ultrafiltration of a milk product containing naturally occurring sialyllactose followed by diafiltration of the ultrafiltration retentate. WO2009/113861 in the name of the applicant relates to a process for isolating sialic-acid-containing oligosaccharides and in particular sialyllactose from a milk stream and especially from a whey stream. The process yields a product having a high content of sialyllactose and a low content of phosphorus compounds. This product is highly suitable for supplementing infant foods. WO 2010/116317 relates to a process of synthesis of sialyl-oligosaccharides and in particular of 6'-sialyllactose and its salts comprising a step of coupling by Koenigs-Knorr reaction under conditions that allow its use on an industrial scale.

Thurl et al. (British J. Nutr. 104:1261-1271, 2010) reported a detailed investigation of the milk oligosaccharide composition of a large number of human milk samples obtained during the first 3 months of lactation. The sialylated oligosaccharides analyzed were 3'-sialyllactose (3'-SL), 6'-sialyllactose (6'-SL), sialyl-lacto-N-tetraoses a-c (LSTa-c) and disialyllacto-N-tetraose (DSLNT). It was found that, besides sialyllactose, DSLNT was the most prominent sialylated oligosaccharide. DSLNT exhibited a maximum time curve 15 days postpartum. Asakuma et al. (Biosci. Biotechnol. Biochem., 71: 1447-1451, 2007) investigated changes in concentration in sialyl-oligosaccharides of human colostrum during the first three days of lactation. Of the colostrum sialyl-oligosaccharides determined, LSTc was present at the highest concentration, followed by DSLNT, 3'-SL and 6'-SL.

Hence, a goal of the present invention is to provide a process for the manufacture of (artificial) disialylated oligosaccharides which can be used as analogs of disialylated HMO's. Preferably, the process can be easily scaled up to generate disialylated oligosaccharides at an industrial scale. Advantageously, said process uses relatively cheap by-products from other kinds of industry, like the meat or dairy industry.

It was surprisingly found that the above goals can be met by decorating galacto-oligosaccharides (GOS) with sialic acids. GOS are oligosaccharides containing multiple galactose (Gal) units, ranging from DP 2-9 and are synthesized from lactose by the enzyme $\beta$-galactosidase. GOS are produced on an industrial scale and have applications in various end-products, such as infant formula and dairy based drinks. Since GOS are not degraded in the human small intestine, they reach the colon largely intact where they serve as prebiotic stimulating growth of beneficial bacteria, like lactobacilli and bifidobacteria. The Gal/Gal linkage type in GOS are (β1-2), (β1-3), (β1-4) and/or (β1-6), depending on the source of the used β-galactosidase. In the case of β-galactosidase from *Bacillus circulans*, yielding Vivinal GOS (FrieslandCampina Domo), the major Gal/Gal linkage type is (β1-4) and to a lesser extent (β1-3) and (β1-6), present in reducing linear and branched oligosaccharides (Table 1). The glucose moiety of GOS may also be connected via an (α1-1β) linkage with a Gal moiety that can be further extended with additional Gal residues (Fransen et al., Carbohydr. Res. 314: 101-114, 1998). The inventors recognized that both the reducing branched oligosaccharides and the non-reducing linear oligosaccharides result in GOS molecules that posses two terminal Gal units and hence two non-reducing ends, each of which can be modified with a sialic acid residue using a sialic acid donor and trans-sialidase (TS) enzyme activity.

TABLE 1

Elucidated GOS structures prepared with *Bacillus circulans* β-galactosidase (Yanahira et al., Biosc. Biotech. Biochem. 59: 1021-1026, 1995; Fransen et al., Carbohydr. Res. 314: 101-114, 1998; Fransen, PhD thesis Utrecht University, 1999; Coulier et al., J. Agr. Food Chem. 57: 8488-8495, 2009

| | |
|---|---|
| Disaccharides | Gal(β1-2)Glc, Gal(β1-3)Glc, Gal(β1-4)Glc, Gal(β1-6)Glc, Gal(β1-3)Gal, Gal(β1-4)Gal, Glc(α1-1β)Gal, Glc(β1-1β)Gal, Gal(β1-4)Fru |
| Trisaccharides | Gal(β1-4)Gal(β1-2)Glc, Gal(β1-4)Gal(β1-3 )Glc, Gal(β1-4)Gal(β1-4)Glc, Gal(β1-4)Gal(β1-6)Glc, Gal(β1-6)Gal(β1-4)Glc, Gal(β1-6)Gal(β1-6)Glc, Gal(β1-2)Glc(α1-1β)Gal, Gal(β1-4)Glc(α1-1β)Gal, Gal(β1-4)Gal(β1-4)Fru Gal(β1-2)[Gal(β1-6)]Glc, Gal(β1-3)[Gal(β1-6)]Glc, Gal(β1-4)[Gal(β1-6)]Glc, Gal(β1-2)[Gal(β1-4)]Glc |
| Tetrasaccharides | Gal(β1-4)Gal(β1-4)Gal(β1-4)Glc, Gal(β1-6)Gal(β1-6)Gal(β1-4)Glc, Gal(β1-4)Gal(β1-4)Glc(α1-1β)Gal, Gal(β1-4)Glc(α1-1β)Gal(4-1β)Gal |
| Pentasaccharides | Gal(β1-4)Gal(β1-4)Gal(β1-4)Gal(β1-4)Glc, Gal(β1-6)Gal(β1-6)Gal(β1-6)Gal(β1-4)Glc, Gal(β1-4)Gal(β1-4)Gal(β1-4)Glc(α1-1β)Gal, Gal(β1-4)Gal(β1-4)Glc(α1-1β)Gal(4-1β)Gal, Gal(β1-4)Glc(α1-1β)Gal(4-1β)Gal(4-1β)Gal |
| Hexasaccharides | Gal(β1-4)Gal(β1-4)Gal(β1-4)Gal(β1-4)Gal(β1-4)Glc, Gal(β1-4)Gal(β1-4)Gal(β1-4)Gal(β1-4)Glc(α1-1β)Gal, Gal(β1-4)Gal(β1-4)Gal(β1-4)Glc(α1-1β)Gal(4-1β)Gal, Gal(β1-4)Gal(β1-4)Glc(α1-1β)Gal(4-1β)Gal(4-1β)Gal, Gal(β1-4)Glc(α1-1β)Gal(4-1β)Gal(4-1β)Gal(4-1β)Gal |

Accordingly, in one embodiment the invention relates to a method for providing a composition comprising sialic-acid-containing oligosaccharides, comprising the steps of:
 a) providing a source of non-digestible galactooligosaccharides containing at least two terminally bound β-linked galactose residues;
 b) providing a sialic acid donor;
 c) contacting said galactooligosaccharide with said sialic acid donor in the presence of an enzyme having trans-sialidase activity in an enzyme reaction mixture; and
 d) obtaining from said enzyme reaction mixture a fraction comprising at least 5 percent by weight of disialylated galactooligosaccharides (di-Sia-GOS) based on the dry matter.

In one embodiment, the source of non-digestible galactooligosaccharide is obtained by enzymatic treatment of lactose with β-galactosidase (EC 3.2.1.23). β-Galactosidase from different sources such as fungi, yeast and/or bacteria, may be used yielding a mixture of oligomers with varied chain lengths and different glycosidic linkage ratios. For example, the commercial galactooligosaccharide preparation Vivinal GOS (FrieslandCampina Domo), comprising 57% GOS, 21% lactose, and 22% glucose and galactose can be used. The GOS part contains in the DP>2 fractions reasonable amounts of reducing branched and non-reducing galacto-oligosaccharides having two terminal galactose units. In one embodiment, a mixture of lactose and α,α-trehalose [Glc(α1-1α)Glc] is treated with β-galactosidase.

The GOS starting material may be pretreated to enrich for those species having two terminally bound β-linked galactose residues. For example, the DP1 and/or DP2 species may be removed prior to trans-sialidase treatment. In another embodiment, a GOS starting composition having a low lactose content (e.g. Vivinal-GOS 90) is suitably used. Individual GOS structures can be separated and isolated from a mixture of GOS species by methods known in the art. For example, nanofiltration can be used as described in Goulas et al. (J. Membr. Sc. 209: 321-335, 2002). In a preferred embodiment, a GOS mixture is fractionated using cation exchange chromatography, preferably wherein the counter ion of the cation exchange resin is potassium. WO2008/041843 discloses methods for isolating various DP fractions from a mixture of GOS species.

Figure 1:
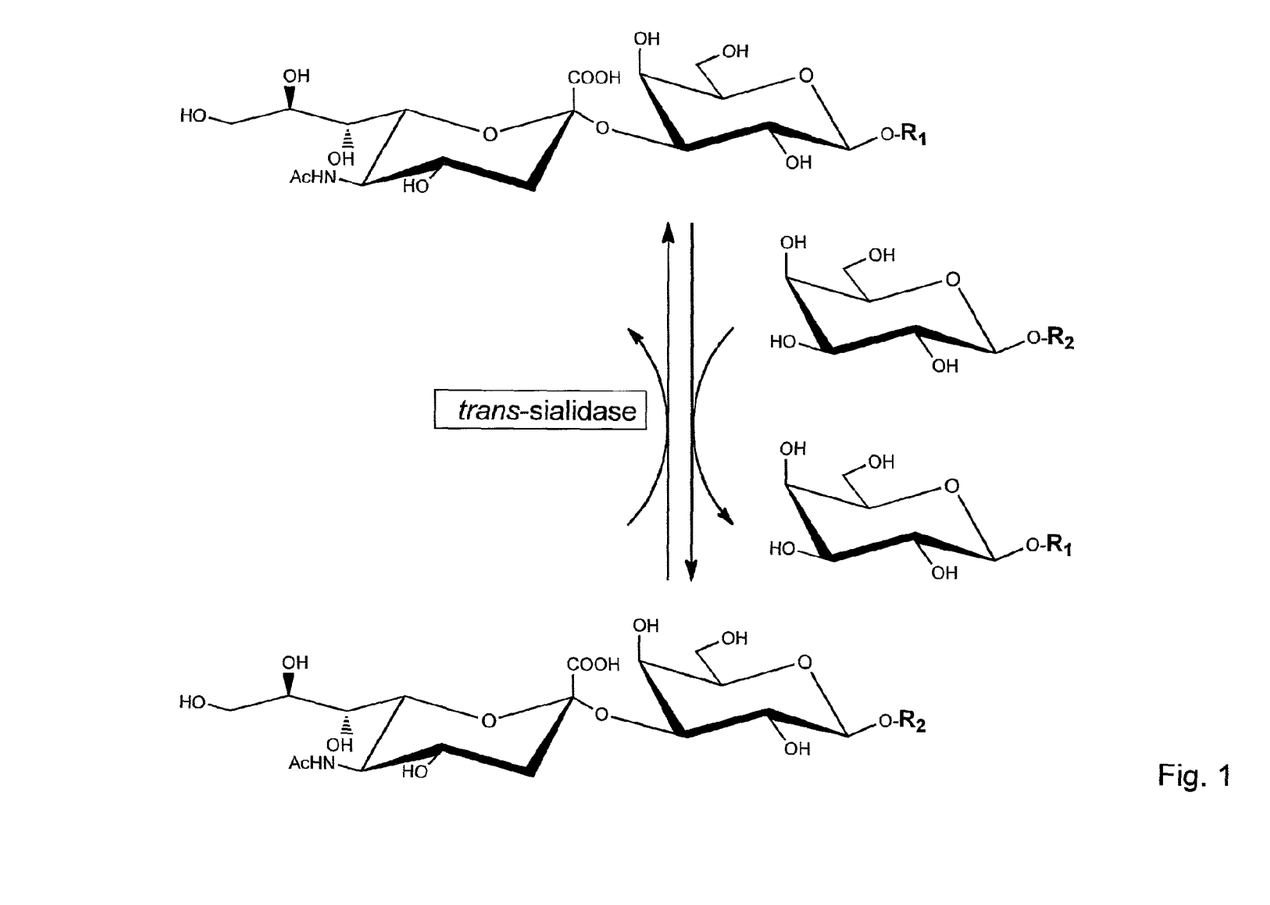
FIG. 1. Reversible trans-glycosylation of ($\alpha$2-3)-linked N-acetylneuraminic acid between Neu5Ac($\alpha$2-3)Gal-OR$_1$ and Neu5Ac($\alpha$2-3)Gal-OR$_2$, catalyzed by trypanosomal trans-sialidases.

Trans-sialidases (FIG. 1) are enzymes with the unique ability to efficiently transfer sialic acids (Neu5Ac or Neu5Gc) from various donors to an acceptor substrate containing terminal β-linked Gal residues. The best studied TS is that from the human parasite *Trypanosoma cruzi* (TcTS), while also TS enzymes are known from closely related *Trypanosoma* species, such as *Trypanosoma brucei* and *Trypanosoma congolense* (Schauer and Kamerling, ChemBioChem 12: 2246-2264, 2011).

TcTS was previously shown to be active towards donor substrates that posses (α2-3)-linked sialic acids only (both Neu5Ac and Neu5Gc) (Scudder et al., J. Biol. Chem. 268: 9886-9891, 1993; Agusti et al., Carbohydr. Res. 342: 2465-2469, 2007). The enzyme has a retaining mechanism, meaning that the products formed also have an (α2-3) bound sialic acid (Scudder et al., 1993). In the absence of a suitable acceptor, TcTS acts as a hydrolase (sialidase), releasing free sialic acid from its substrates. Because of its sialic acid transferring capabilities and broad substrate range (both donor and acceptor), the TcTS enzyme is widely used in glycobiology to synthesize sialylated oligosaccharides (e.g. Neubacher et al., Org. Biomol. Chem. 3: 1551-1556, 2005). Other enzymes capable of transferring sialic acid to acceptor molecules are sialyltransferases. These enzymes, however, require activated sialic acid (CMP-Neu5Ac). Since nucleotide sugars are expensive, sialyltransferases are less suitable for (large-scale) applications in glycobiology.

The enzymatic sialylation with trans-sialidases of acceptor molecules is known in the art. See US2007/0004656, disclosing a novel enzyme isolated from *Trypanosoma congolese* and the application thereof to produce sialylated products for use in vaccines, medicaments, foodstuffs or food additives. Although GOS are included in the list of possible sialic acid acceptors, the generation and isolation of a fraction enriched in disialylated products is not disclosed or suggested. In fact, the present observation that trans-sialylation of GOS results not only in monosialylated GOS (mono-Sia-GOS) but also in disialylated species (di-Sia-GOS) has heretofore never been reported.

The degree of polymerization (DP) of the di-Sia-GOS species obtainable according to the invention will of course depend on the DP or range of DPs of the GOS acceptor molecules used. As said, typical GOS preparations contain oligosaccharides ranging between DP 2 and 8. For Vivinal GOS, the mixture can roughly be described as Gal(β1-x)Gal(β1-x) . . . Gal(β1-x)Glc (major amount; reducing linear and branched (DP>2) GOS components) with x=4 (mainly), 3, and 6; and Gal(β1-4)Gal(β1-4) . . . Gal(β1-4)Glc(α1-1β)Gal(4-1β) . . . Gal(4-1β)Gal (minor amount; non-reducing GOS components) (Table 1).

In one embodiment, a method of the invention comprises isolation of a fraction comprising at least 5 percent by weight, preferably at least 7, 10, 12, 18, 20, 22, 25, 27 or 30% by weight of di-Sia-GOS based on the dry matter, wherein said di-Sia-GOS have a degree of polymerization (DP) within the range of DP5 to DP11, preferably DP6 to DP8.

Exemplary disialylated GOS structures that can be formed based on
Table 1, include the following:
Pentasaccharide from GOS DP3
Neu5Ac(α2-3)Gal(β1-4)Glc(α1-1β)Gal(3-2α)Neu5Ac
Neu5Ac(α2-3)Gal(β1-2)[Neu5Ac(α2-3)Gal(β1-6)]Glc
Neu5Ac(α2-3)Gal(β1-3)[Neu5Ac(α2-3)Gal(β1-6)]Glc,
Neu5Ac(α2-3)Gal(β1-4)[Neu5Ac(α2-3)Gal(β1-6)]Glc
Neu5Ac(α2-3)Gal(β1-2)[Neu5Ac(α2-3)Gal(β1-4)]Glc
Hexasaccharides from GOS DP4
Neu5Ac(α2-3)Gal(β1-4)Gal(β1-4)Glc(α1-1β)Gal(3-2α)Neu5Ac
Neu5Ac(α2-3)Gal(β1-4)Glc(α1-1β)Gal(4-1β)Gal(3-2α)Neu5Ac
Heptasaccharides from GOS DP5
Neu5Ac(α2-3)Gal(β1-4)Gal(β1-4)Gal(β1-4)Glc(α1-1β)Gal(3-2α)Neu5Ac
Neu5Ac(α2-3)Gal(β1-4)Gal(β1-4)Glc(α1-1β)Gal(4-1β)Gal(3-2α)Neu5Ac
Neu5Ac(α2-3)Gal(β1-4)Glc(α1-1β)Gal(4-1β)Gal(4-1β)Gal(3-2α)Neu5Ac
Octasaccharides from GOS DP6
Neu5Ac(α2-3)Gal(β1-4)Gal(β1-4)Gal(β1-4)Glc(α1-1β)Gal(3-2α)Neu5Ac
Neu5Ac(α2-3)Gal(β1-4)Gal(β1-4)Gal(β1-4)Glc(α1-1β)Gal(4-1β)Gal(3-2α)Neu5Ac
Neu5Ac(α2-3)Gal(β1-4)Gal(β1-4)Glc(α1-1β)Gal(4-1β)Gal(4-1β)Gal(3-2α)Neu5Ac
Neu5Ac(α2-3)Gal(β1-4)Glc(α1-1β)Gal(4-1β)Gal(4-1β)Gal(4-1β)Gal(3-2α)Neu5Ac In view of the enzyme specificity of the trans-sialidase used, the term "sialic acid donor" refers to any compound having one or more (α2-3)-sialylated glycans (glycoproteins, glycopeptides, glycolipids) or synthetic sialic acid glycosides (e.g. 2'-(4-methylumbelliferyl)-α-N-acetylneuraminic acid (4MU-Neu5Ac) (Schauer and Kamerling, ChemBioChem 12: 2246-2264, 2011). These include (α2-3)-linked N-acetylneuraminic acid (Sia=Neu5Ac) donors and (α2-3)-linked N-acetylneuraminic acid/N-glycolylneuraminic acid (Sia=Neu5Ac/Neu5Gc) donors. For human applications, preferably, the sialic acid donor contains (α2-3)-linked Neu5Ac, but for feed applications, the sialic acid donors may contain (α2-3)-linked Neu5Ac/Neu5Gc. Combinations of different donors may also be used.

In one embodiment step b), the sialic acid donor is a naturally occurring compound, preferably selected from sialic acids bound to oligosaccharides, polysaccharides, polysialic acids, glycoproteins. For example, the sialic acid donor is selected from whole animal blood plasma or bloodplasma-derived glycoproteins, being typical products of the slaughterhouse, and milk glycoproteins from the dairy industry, or glycolipids. Milk glycoproteins occur in a large variety in cow milk. The N- and O-linked carbohydrate chains are frequently terminated with members of the sialic acid (Sia) family. For example, the sialic acid donor is selected from the group consisting of glycosylated whey proteins and caseins, and fragments of the same.

A highly advantageous sialic acid donor for use in the present invention is glycomacropeptide (GMP) from κ-casein, which is produced as a by-product in the dairy industry. GMP is decorated with O-glycans, containing both Neu5Ac(α2-3)Gal(β1- and Neu5Ac(α2-6)GalNAc(α1-units (van Halbeek et al., Biochim. Biophys. Acta 623: 295-300, 1980). With GMP as (α2-3)-linked N-acetylneuraminic acid (Sia=Neu5Ac) donor in a method of the invention, the resulting di-Sia-GOS will find its way in among others infant nutrition and functional food.

In another preferred embodiment, the sialic acid donor is selected from the group consisting of glycosylated animal mucus proteins, and fragments of the same. Animal mucins are glycoproteins with a relatively high carbohydrate content. The O-linked carbohydrate chains are frequently terminated with members of the sialic acid (Sia) family, of which N-acetylneuraminic acid (Neu5Ac) and N-glycolylneuraminic acid (Neu5Gc) are the most important ones. Different mucins can have different sialylation patterns. Of particular interest are pig and cow small intestinal mucin glycoproteins, typical by-products of the slaughterhouse, as sialic-acid-containing material. For instance, according to the literature, the sialylation pattern of pig small intestinal mucin glycoprotein (PSMG) comprises Neu5Ac(α2-3)Gal(β1-, Neu5Gc(α2-3)Gal(β1-, Neu5Ac(α2-6)GalNAc(α1-, and Neu5Gc(α2-6)GalNAc(α1-units (Hansson et al., Carbohydr. Res. 221: 179-189, 1991). With PSMG as (α2-3)-linked N-acetylneuraminic acid/N-glycolylneuraminic acid (Sia=Neu5Ac/Neu5Gc) donor, the resulting di-Sia-GOS will find its way among others in the animal feed industry.

For example, the sialic acid donor is obtained from mucin in a production process whereby pig intestines are cleaned for the production of casings (removal of unborn manure; pressing mucin, pressing the caul, further processing of casing), followed by concentration and/or further purification/enzymatic degradation of sialic-acid-containing mucin biopolymers.

Thus, in one embodiment the invention involves enzymatic trans-glycosylation using a sialic acid donor obtained from relatively cheap by-products from the slaughterhouse and the dairy industry to upgrade functional food.

In one embodiment step c) of a method disclosed herein uses an enzyme having trans-sialidase activity which is encoded by a gene product from microorganisms of the Trypanosoma genus, preferably Trypanosoma cruzi or Trypanosoma congolense. Preferably, said enzyme is recombinantly produced in a host cell e.g. a bacterial host cell like E. coli.

The incubation conditions can vary depending on the enzyme source. In one embodiment using TcTS, the pH of the enzyme reaction mixture ranges between 4 and 6, preferably between 4.8 and 5.8. Preferred buffers include Na-citrate, Pipes and TrisHCl, and mixtures thereof. In one embodiment, the enzyme incubation is performed in a mixture of Na-citrate, Pipes and Tris-HCl (25 mM each) pH 5.5. It is also possible to carry out the enzyme reaction in an aqueous solution. For example, incubation of TcTS with GMP and GOS in water gave the same high conversion as observed for Na-citrate at pH 5.0. The enzyme may be stabilized by protein components, for example bovine serum albumin, but in the case of using glycoprotein donors this is not necessary.

As the sialic acid transfer from donor to acceptor will not be complete, a mixture of GOS, sialylated GOS, sialic acid donor and asialo-donor can in theory be formed. For example, in case Vivinal GOS is applied as source of GOS, the product mixture will contain GOS, sialylated-GOS, lactose, galactose, glucose, and sialyllactose (lactose is also an acceptor for sialic acid). In case of GMP, Sia stands for Neu5Ac, in case of PSMG for Neu5Ac/Neu5Gc. This mixture may be separated via centrifugal filtration (spin filters) into a high-molecular glycoprotein/enzyme fraction and a low-molecular carbohydrate fraction prior to the step of isolated a fraction enriched in disialylated GOS. In principle, the Neu5Ac/Neu5Gc mixture can be separated in its Neu5Ac and Neu5Gc components via lectin or antibody chromatography.

Step d) of a method of the invention comprises isolating from said enzyme reaction mixture a fraction comprising at least 5 percent by weight of disialylated galactooligosaccharides based on the dry matter. Since disialylated oligosaccharides have two negative charges per molecule at a physiological pH, they are suitably isolated using a separation technique based on a difference in charge between components to be separated, such as preferably anion-exchange chromatography. Exemplary anion-exchange resins include Resource Q. For example, after 21 h of incubation of GOS DP5 with TcTS and 4MU-Neu5Ac as artificial donor, the mixture can be separated in a neutral GOS DP5, a mono-Sia-GOS DP5 (monosialylation of the reducing linear and branched as well as the non-reducing GOS components of DP5), a free Sia, and a di-Sia-GOS DP5 fraction (disialylation of the reducing branched and non-reducing GOS components of DP5), as checked by MALDI-TOF-MS and NMR spectroscopy after desalting.

Other suitable separation techniques are based on a difference in size between components to be separated, preferably size-exclusion chromatography.

Depending on the separation procedure employed and the intended application, the di-Sia-GOS enriched fraction may be subjected to a further clean-up treatment, e.g. a desalting procedure in case anion-exchange chromatography has been used.

A further embodiment relates to a composition comprising at least 5 percent by weight of disialylated galactooligosaccharides, obtainable by a method according to the invention. The composition preferably comprises at least 7, 10, 12, 18, 20 22, 25, 27 wt %, more preferably at least 30 wt % of disialylated galactooligosaccharides. In one embodiment, the composition comprises less than 80 wt %, preferably less than 60 wt % of mono-sialylated oligosaccharides. The weight ratio of di-sialylated to mono-sialylated oligosaccharides is for example between 1:20 and 100:1, more preferably between 1:10 and 9:1. In another preferred embodiment, the composition is essentially devoid of mono-sialylated oligosaccharides. The composition preferably does not contain (active) enzyme.

Also provided is the use of a composition enriched in disialylated galactooligosaccharides as active ingredient, for example as nutritional, pharmaceutical or nutraceutical additive.

In one embodiment, the invention provides a nutritional product comprising a composition enriched in disialylated galactooligosaccharides obtainable as described herein. Besides the di-Sia-GOS species the food product may comprise other oligosaccharides, in particular prebiotic oligosaccharides and oligosaccharide mixtures. The addition of probiotics is also envisaged.

The nutritional product can be for human or animal purposes. For human applications, the presence of high concentrations of Neu5Gc should be prevented since Neu5Gc does not or hardly occur in humans. Hence, for use in human products it is preferred to use a (α2-3)-linked N-acetylneuraminic acid (Sia=Neu5Ac) donor as sialic acid donor, for example GMP. In case of using a sialic acid donor with (α2-3)-linked N-acetylneuraminic acid/N-glycolylneuraminic acid (Sia=Neu5Ac/Neu5Gc), for example PSMG, the Neu5Gc-containing GOS species should be removed e.g. by lectin chromatography. In a specific aspect, the nutritional product is an infant formula. For example, a fraction enriched in di-Sia-GOS wherein Sia is Neu5Ac is added as supplement to a conventional infant formula in order to more closely resemble the composition of human milk, thereby enhancing the beneficial properties of the formula. With the di-Sia-GOS concentrate of the present invention, infant formulas can be enriched with disialylated oligosaccharides in concentrations matching human milk, i.e. the concentration of disialylated oligosaccharides can be increased to 200-500 mg/l matching concentrations of human milk of various lactation stages. Of course, the concentrate is also suitably used to bring the total concentration of oligosaccharide bound sialic acid to 100-1500 mg/l. However, the scope of the present invention is not limited to this range of enrichment due to the great variations in human milk composition and also due to the fact that other (food) applications may require other oligosaccharide bound (di)sialic acid concentrations. In the present invention sialylated oligosaccharide concentrations have been measured using high performance liquid chromatography (HPLC) equipped with a UV detection system and a Resource Q column, however and state of the art technique with acceptable accuracy may be employed.

The di-Sia-GOS fraction of the invention can be used as such, or it can be further treated by for example reverse osmosis, crystallisation, affinity chromatography or a combination there of to remove water and/or salts, or it can be dried alone or together with one or more carriers. Any carrier can be used, such as oil, fat, whey, demineralised whey, whey protein concentrate, whey protein isolate, other whey fractions, whey or milk permeate or concentrate, skimmed milk, whole milk, semi-skimmed milk, milk fractions, maltodextrins, sucrose, lactose, native and pregelatinised starches, glucose syrups, casein and casein fractions.

The di-Sia-GOS fraction of the invention, including a dried concentrate thereof, can be used in any nutritional compositions, such as products for infant nutrition, protein bars, sports nutrition, drinks, health supplements, food for medical purposes and clinical nutrition. Infant nutrition can be, but is not restricted to, infant formulas, follow-on formulas, infant cereal products or growing-up milk, i.e. modified milk or milk powder suitable for children of 1-3 years.

Such formula is particularly suitable for administration to pre-term infants since the di-Sia-GOS enriched fraction may help to combat infections by harmful micro-organisms, including protozoa such as *Entamoeba histolytica* the parasite that causes Amebiasis. In one embodiment, the di-Sia-GOS fraction is used to protect the body from infection by inhibiting the adhesion of a microbial pathogen to human intestinal epithelial cells. For example, it is used to block binding of *E. histolytica* to host cells through interaction with the parasite's Gal/GalNAc-lectin, a major virulent protein that mediates adhesion and cytotoxicity. Hence, also encompassed is a method for providing an infant formula, comprising isolating a fraction comprising at least 50 percent by weight of disialylated galactooligosaccharides based on the dry matter and formulating said fraction into an infant formula together with a protein source, a fat source, a carbohydrate source and other conventional ingredients such as vitamins and minerals. Therapeutically or prophylactically effective amounts will depend on various factors e.g. age and body weight of the subject to be treated, the disease to be prevented or treated, the type of dosage form and the like.

The invention also relates to the medical use of a composition comprising a di-Sia-GOS fraction as disclosed herein. For instance, it is suitably used in a method of treating or preventing necrotizing enterocolitis (NEC) in a subject, preferably a human subject, more preferably a preterm infant. NEC is a serious bacterial infection in the intestine, primarily of sick or premature newborn infants. It can cause the death (necrosis) of intestinal tissue and progress to blood poisoning (septicemia). It has a high mortality rate, especially among very low birth weight babies. Some 20 to 40 percent of these infants die. NEC develops in approximately 10% of newborns weighing less than 800 g (under 2 lbs). Necrotizing enterocolitis almost always occurs in the first month of life. Infants who require tube feedings may have an increased risk for the disorder. Hence, the risk for necrotizing enterocolitis may be diminished by using an enteral nutrition comprising a di-Sia-GOS-containing formula as provided herein.

For animal applications, the presence of high concentrations of Neu5Gc does not form a problem. It can even be an advantage, as it has been reported that especially Neu5Gc-containing compounds are effective in the battle against specific infections leading to diarrhoea in piglets and calves. Hence, for use in animal feed products it is preferred to use a donor comprising ($\alpha$2-3)-linked N-acetylneuraminic acid and N-glycolylneuraminic acids (Sia=Neu5Ac/Neu5Gc), such as PSMG. Provided herein is an animal feed product comprising a composition enriched in di-Sia-GOS wherein Sia is Neu5Ac and/or Neu5Gc, preferably Neu5Ac and Neu5Gc. The feed product is preferably formulated for piglets or calves and may comprise one or more further beneficial ingredients to enhance animal performance, meat quality and animal health.

EXPERIMENTAL SECTION

Example 1

Heterologous Expression and Purification of *Trypanosoma Cruzi* Trans-Sialidase (TcTS)

A DNA clone of TcTS containing a N-terminal 6xHis-tag was obtained from Professor A. C. C. Frasch (Buenos Aires, Argentina). To express the protein, the growth and induction conditions as described in the literature (Paris et al., Glycobiology 11: 305-311, 2001) were slightly modified. Construct pTrcTS611/2 was transformed into *E. coli* TOP10 or BL21(DE3) and cultures were inoculated in terrific broth medium, supplemented with ampicillin (100 μg/ml) and 0.1 mM isopropyl β-D-1-thiogalactopyranoside (IPTG) as inducer. The medium was inoculated directly from fresh colonies from Luria Bertani agar plates, then incubated for 24 h at 30° C. (OD600 of 0.6) with shaking (200 rpm). After harvesting the cells, the pellets were resuspended in lysis buffer (bacterial protein extraction reagent/B-PER), and allowed to lyse at room temperature according to the manufacturer's protocol. Cell debris was removed by ultracentrifugation for 30 min at 40,000 g, and the supernatant was subjected to gravity flow Ni$^{2+}$-nitrilotriacetic acid (NTA) column affinity chromatography. The recombinant TcTS was eluted from the column using 100 mM imidazole, yielding an enzyme preparation that was not completely pure (SDS-PAGE). But, as it is known that the enzyme becomes instable in purified form (Turnbull et al., Tetrahedron 58: 3207-3216, 2002), further purification steps were omitted.

Example 2

Activity Tests and Kinetic Studies of TcTS Preparations

Activity assays with partially purified TcTS (2 mU/ml) were conducted with 1 mM 2'-(4-methylumbelliferyl)-α-N-acetylneuraminic acid (4MU-Neu5Ac) as commercial synthetic sialic acid model donor and lactose as acceptor, with subsequent formation of the product Neu5Ac($\alpha$2-3)lactose (3'-sialyllactose, 3'SL). In the presence of a 10-fold excess of lactose, nearly 80% of the Neu5Ac unit of 4MU-Neu5Ac was transferred to lactose.

In kinetic experiments with partially purified TcTS, 4MU-Neu5Ac or industrially available κ-casein-derived glycomacropeptide (GMP) as donors and lactose as acceptor, the formation of 3'SL was quantitatively determined after 15 and 30 min of incubation, making use of high-pH anion-exchange chromatography with pulsed amperometric detection (HPAEC-PAD). For both donors, the optimal temperature for the transfer reaction, deduced from a series of temperatures ranging from 15-50° C., with increments of 5° C., turned out to be 25° C., which is similar to the optimal temperature reported in literature (Scudder et al., J. Biol. Chem. 268: 9886-9891, 1993).

With respect to the thermal stability of TcTS, estimated in the range 15-50° C. with 5° C. intervals (30 min treatments; remaining activity determined at 25° C.), the enzyme retained its full activity until 25° C. and then steadily decreased. After incubation at 50° C. only 6% of the initial activity remained.

When using 4MU-Neu5Ac as donor, the addition of protein (BSA) has a stabilizing effect on the TcTS activity; when using GMP, the addition of BSA is not necessary.

The optimal pH for the transfer reaction, as deduced from incubations of TcTS, 4MU-Neu5Ac, and lactose (25° C.) in 50 mM sodium citrate buffers (pH 4.5, 5.0, 5.5), Pipes buffers (pH 6.0, 6.5, 7.0, 7.5), and Tris-HCl buffers (pH 8.0, 8.5, 9.0) in the presence of BSA, turned out to be pH 5.0. A determination independent on the buffer type, as deduced from incubations using mixed buffers, containing 25 mM sodium citrate, Pipes, and Tris-HCl, ranging from pH 4.5 to 9.0, led to an optimal pH of 5.5.

The affinity of TcTS for the sialic acid donor substrates 4MU-Neu5Ac and GMP was tested by performing incubations (4.5 mU/ml) with an appropriate range of these substrates and a fixed concentration of lactose as acceptor. For 4MU-Neu5Ac the incubation mixtures contained 0.1, 0.25, 0.5, 1.0, 2.5, 5.0 and 10.0 mM 4MU-Neu5Ac and 1 mM lactose; the $K_m$ was found to be 1.65 mM and the Vmax 1.5 U/mg. For GMP the incubation mixtures contained 0.01, 0.025, 0.05, 0.075, 0.1, 0.25, 0.5, 1.0, 2.5, and 5.0 mM GMP and 5 mM lactose; the $K_m$ was found to be 0.18 mM and the Vmax 3.0 U/mg.

Example 3

Analysis of the Sialic Acid Specifications of the Donor GMP

Mild acid hydrolysis of GMP (MW=10 kDa), using 0.1 M HCl (1 h; 80° C.), followed by quantitative analysis of the released sialic acids by HPAEC-PAD, yielded a sialic acid content of 4.4%, built up from 99% Neu5Ac and 1% Neu5Gc.

From the literature it is known that the O-glycans of GMP contain an array of oligosaccharides with both (α2-3)- and/or (α2-6)-linked sialic acid (van Halbeek et al., Biochim. Biophys. Acta 623: 295-300, 1980). Of these two linkage positions, only the (α2-3)-linked sialic acid acts as an effective donor for TcTS (Schauer and Kamerling, ChemBioChem 12: 2246-2264, 2011). The amount of (α2-3)-linked Neu5Ac, as determined by incubation with the (α2-3)-specific sialidase from Salmonella typhimurium, followed by HPAEC-PAD analysis, turned out to be 72%.

TcTS (8 mU/ml) incubations with GMP (sialic acid content: 4.4%; 1 mM total sialic acid, (α2-3)- and (α2-6)-linked) and 10 mM lactose resulted in the transfer of around 60% of the total Neu5Ac into 3'SL (HPAEC-PAD) (t=0 h: 0% 3'SL, 0% free Neu5Ac; t=1 h: 42% 3'SL, 0% free Neu5Ac; t=2 h: 53% 3'SL, 0% free Neu5Ac; t=4 h: 58% 3'SL, 0% free Neu5Ac; t=24 h: 51% 3'SL, 5% free Neu5Ac). Taking into account the linkage specificity, the actual conversion efficiency of (α2-3)-linked Neu5Ac into 3'SL is 81% at t=4 h.

Example 4

Figure 2:
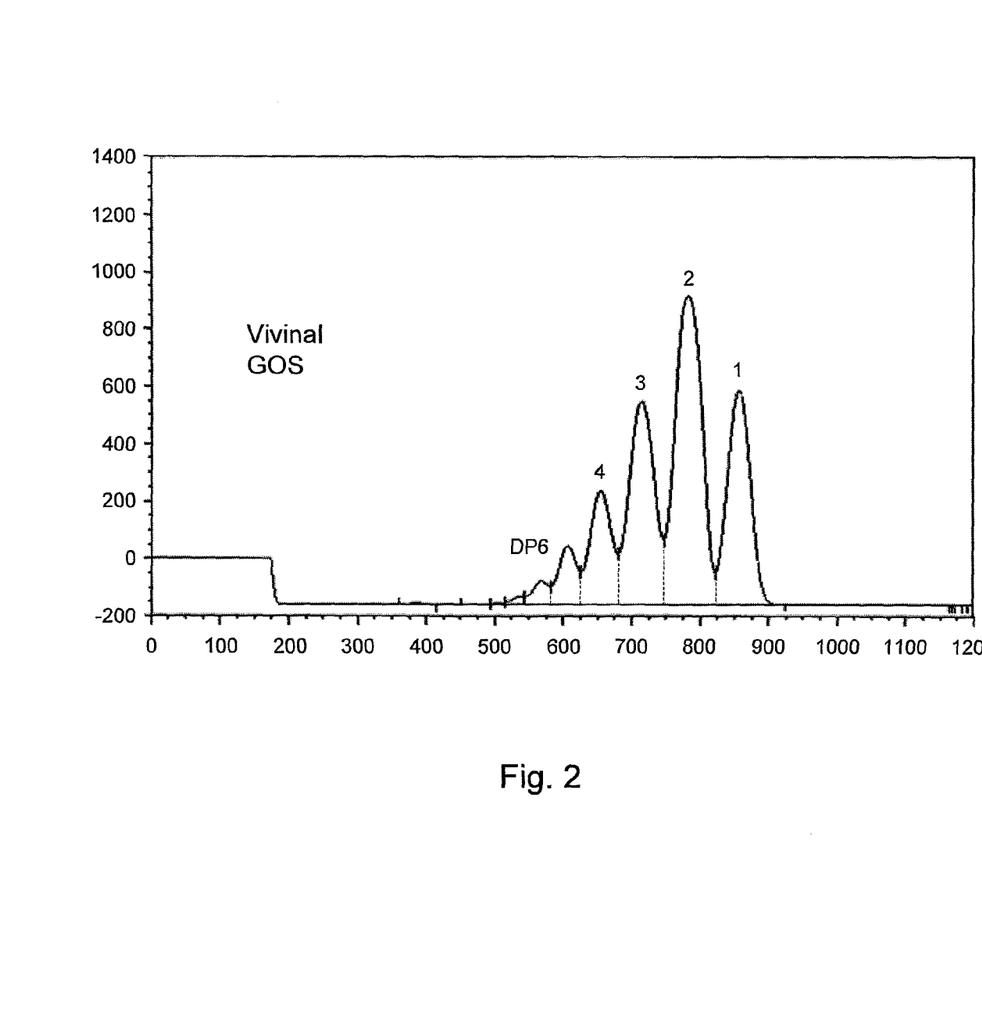
FIG. 2. Separation of Vivinal-GOS on Bio-Gel P2 into 8 fractions of different DP. Demi water was used as eluent at a flow rate of 1 ml/min at 40° C.

Evaluation of Sialylated Products Obtained with Acceptor Vivinal-GOS and 4MU-Neu5Ac as Donor Commercially available Vivinal-GOS, being a mixture of 57% galacto-oligosaccharides (GOS) with different degrees of polymerization (DP), i.e. 57% GOS, 21% lactose, and 22% galactose+glucose, was separated into the DP fractions 2-8 on Bio-Gel P2 (FIG. 2). The fractions were checked by MALDI-TOF-MS analysis, demonstrating separate GOS DP pools, with low contamination of the adjacent DP's.

Figure 3:
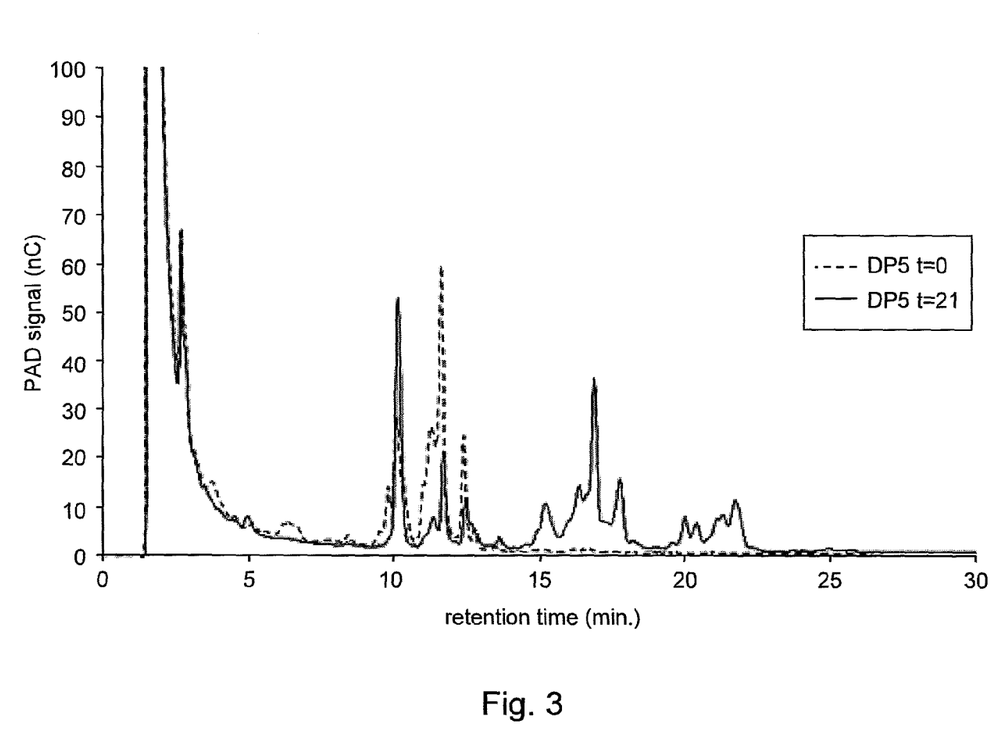
FIG. 3. HPAEC-PAD profiles of a TcTS incubation of GOS DP5 with 4MU-Neu5Ac at t(0)(dotted line) and after 21 h of incubation (solid line), showing the formation of monosialylated GOS DP5 (15-18 min) and disialylated GOS DP5 (20-23 min).

Recombinant TcTS incubations (2 mU/ml) were conducted with GOS DP2 to GOS DP6 as acceptor substrate (3 mmol) and 4MU-Neu5Ac as donor substrate (6 mmol). Besides reducing linear oligosaccharides, parts of DP3 to DP6 are reducing branched and non-reducing linear oligosaccharides, containing two terminally bound β-linked galactose (Gal) residues (Table 1). As demonstrated by HPAEC-PAD, in all cases product formation could be observed, accompanied with a decrease of the GOS substrates. The sialylated GOS products of the higher DPs consist, besides starting material, of two charged pools, a major monosialylated pool and a minor disialylated pool. As a typical example, in FIG. 3, the results for GOS DP5 are depicted. The chromatogram shows a major charged pool with retention times between 15 and 20 min, and a minor charged pool with retention times between 20 and 22 min. Further structural analysis of these pools demonstrated the occurrence of monosialylated GOS DP5 (mono-Sia-GOS DP5) and disialylated GOS DP5 (di-Sia-GOS DP5) (Sia=Neu5Ac).

Example 5

Figure 4:
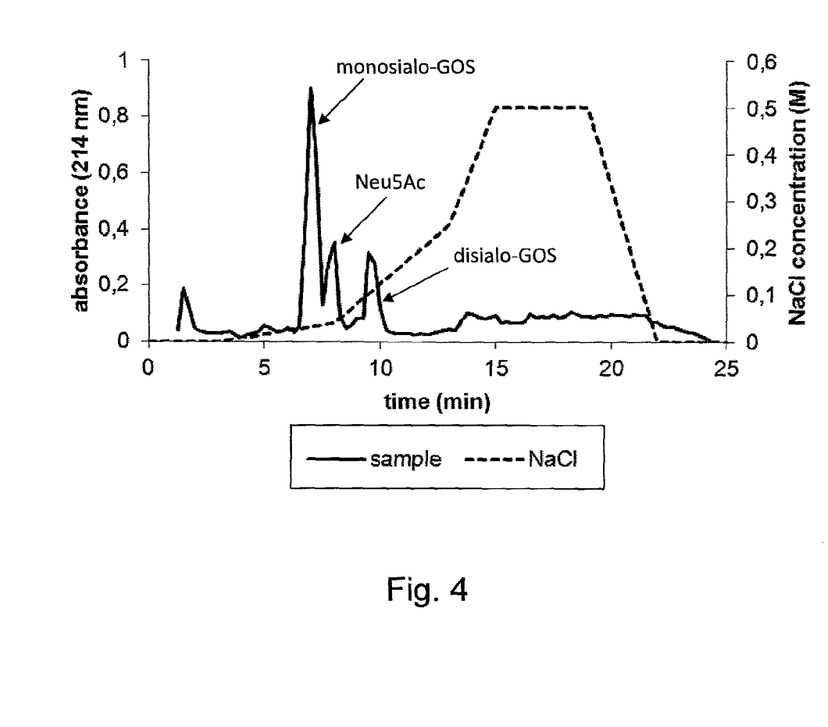
FIG. 4. Separation of sialylated GOS DP5 on Resource Q, using a NaCl gradient and monitored at 214 nm.

TcTS-Catalyzed Incubation of Vivinal-GOS DP5 and 4MU-Neu5Ac, Analyzed by $^1$H NMR Spectroscopy For $^1$H NMR analysis, TcTS (2 mU/ml) was incubated with Vivinal-GOS DP5 (1 mmol) and 4MU-Neu5Ac (2 μmol) for 16 h at 25° C. and pH 5. The monocharged and dicharged fractions were collected via anion-exchange chromatography (FIG. 4), aliquots of which were analyzed by HPAEC-PAD for verification.

Figure 5:
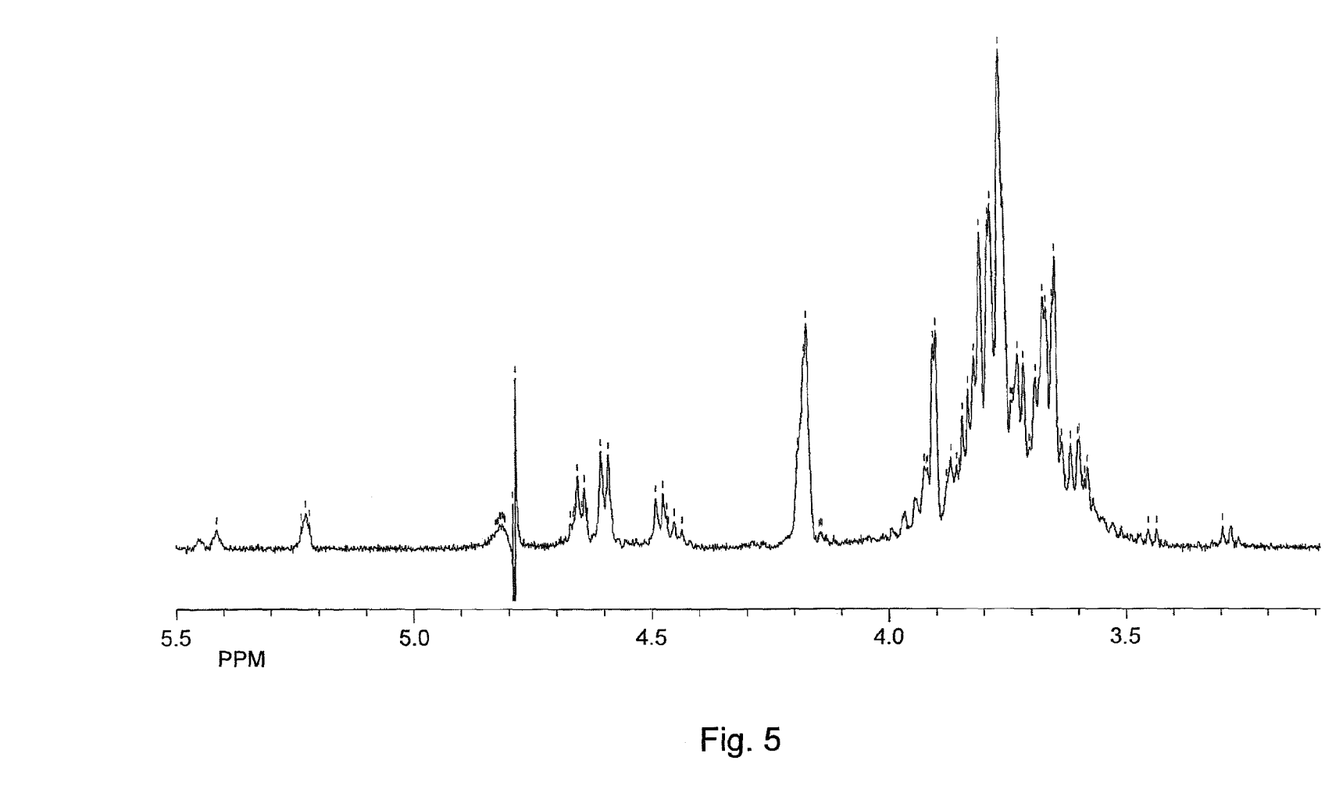
FIG. 5. 500 MHz $^1$H NMR spectrum of Vivinal-GOS DP5.
Figure 6:
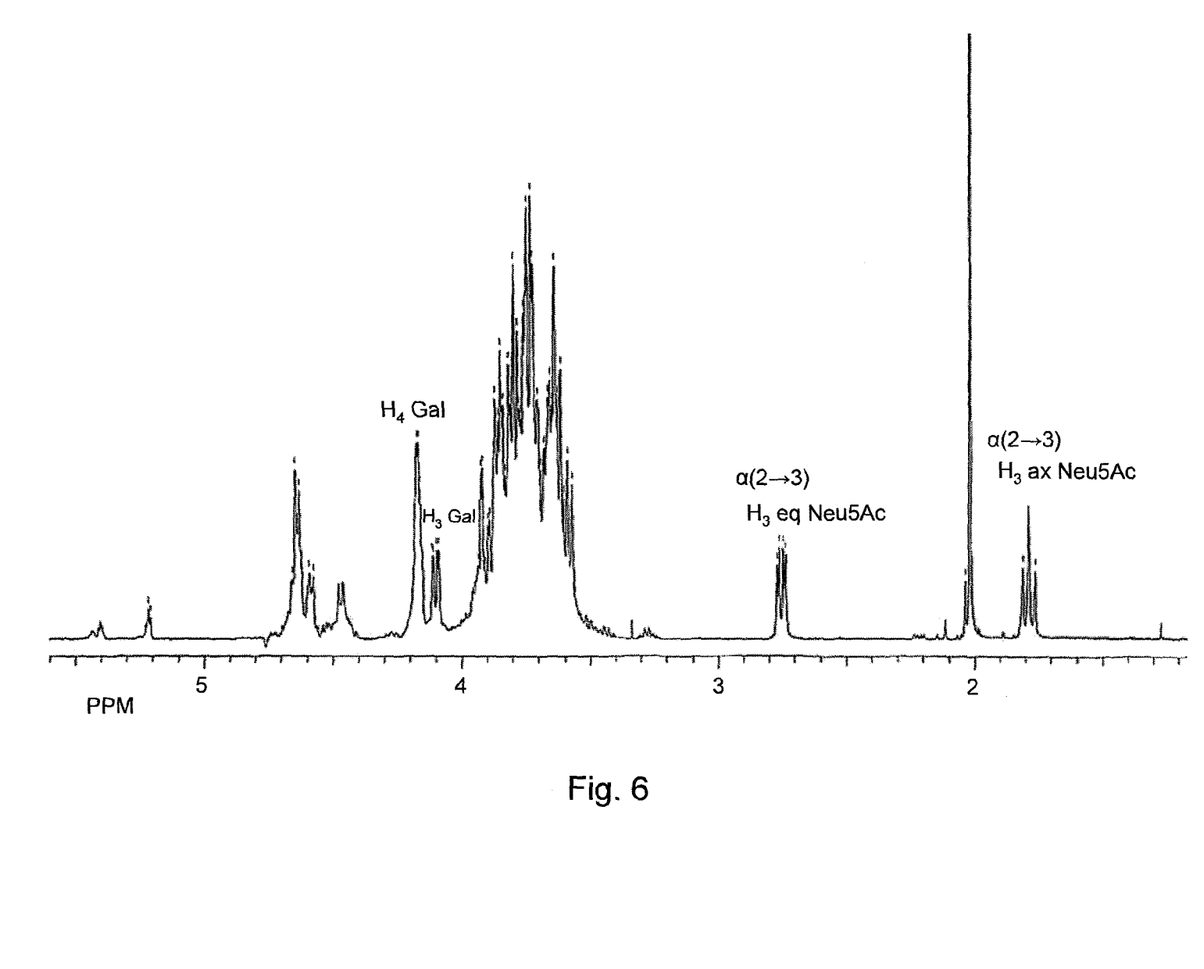
FIG. 6. 500 MHz $^1$H NMR spectrum of mono-Sia-GOS DP5.
Figure 7:
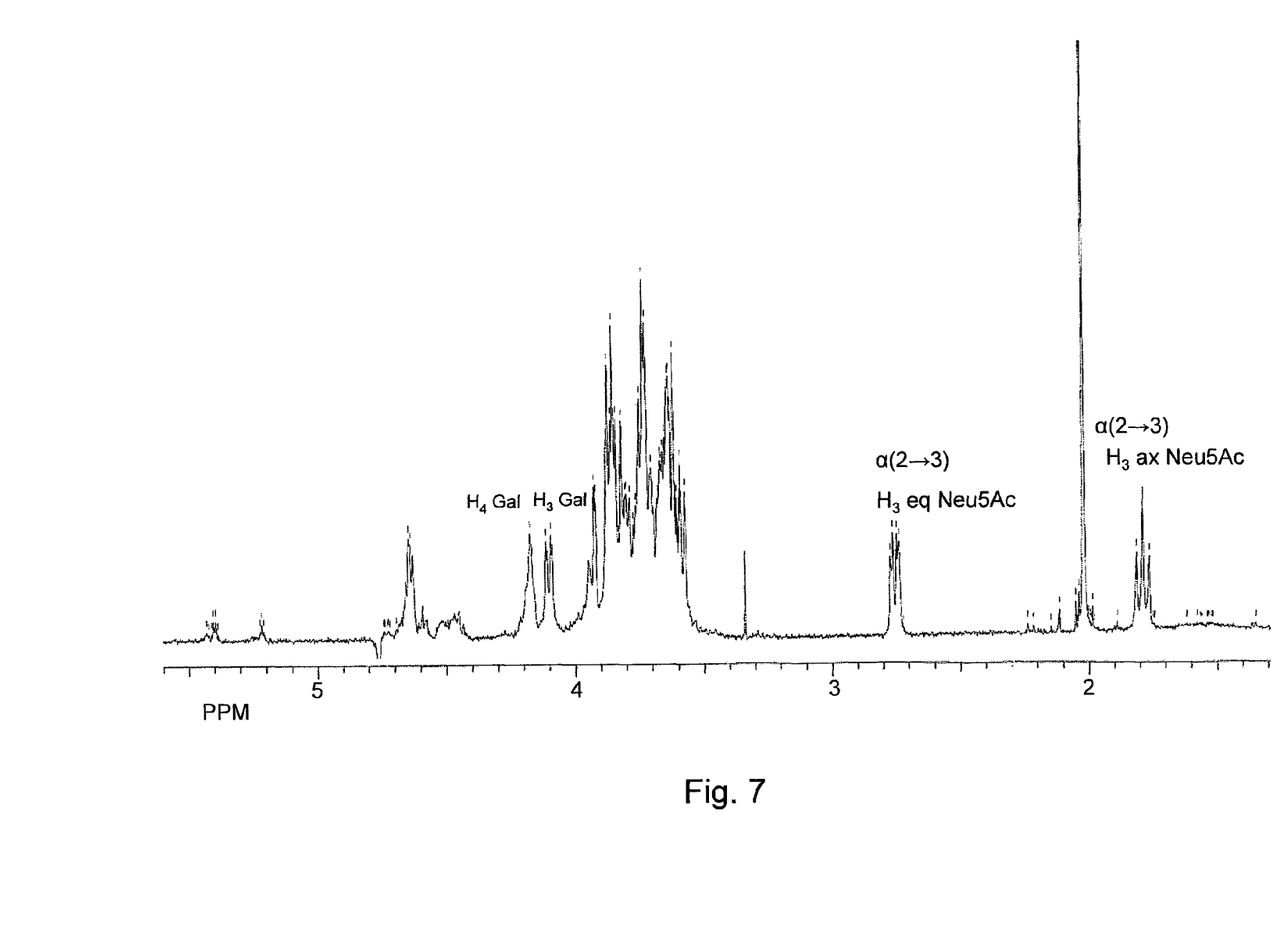
FIG. 7. 500 MHz $^1$H NMR spectrum of di-Sia-GOS DP5.

FIGS. 5, 6, and 7 present the $^1$H NMR spectra of GOS DP5, mono-Sia-GOS DP5, and di-Sia-GOS DP5 (Sia=Neu5Ac), respectively. In earlier studies (Fransen et al., Carbohydr. Res. 314: 101-114, 1998) it has been shown that the major components of GOS DP5 comprise the following structures (the 4-substituted Gal residues dominate over the 6-substituted ones):

Gal(β1-4)Gal(β1-4)Gal(β1-4)Gal(β1-4)Glc
Gal(β1-6)Gal(β1-6)Gal(β1-6)Gal(β1-4)Glc
Gal(β1-4)Gal(β1-4)Gal(β1-4)Glc(α1-1β)Gal 
Gal(β1-4)Gal(β1-4)Glc(α1-1β)Gal(4-1β)Gal
Gal(β1-4)Glc(α1-1β)Gal(4-1β)Gal(4-1β)Gal

However, as shown in example 10, also reducing branched structures do occur (see examples 8 and 9 for the occurrence of reduced branched structures in GOS DP3 and DP4).

The spectra of the sialylated GOS DP5 probes reflect the presence of (α2-3)-linked Neu5Ac only. Based on the surface ratios of the Gal H-3 and H-4 and the Neu5Ac H-3e and H-3ax signals, the assignment for the mono-Sia-GOS DP5 and di-Sia-GOS DP5 pools could be made. Based on the UV responses on Resource Q, the molar ratio of mono-Sia-GOS DP5 and di-Sia-GOS DP5 is about 8.5:1.

Example 6

Analysis of the Sialic Acid Specifications of the Donor PSMG

Small intestines were retrieved from casing material, cleaned by means of pressing and washing in water of 44-48° C.

The mucus is subsequently pressed out the small intestines in 2 or 3 steps, depending on equipment installed, at increasing pressures. The final step of the cleaning process is to remove the mucus membrane.

The mucus resulting from these pressing steps is collected and an aqueous solution of sodium meta bisulphite is added.

Mild acid hydrolysis of industrially available pig small intestinal mucin glycoprotein (PSMG) material (MW=1.7× $10^3$ kDa), using 0.1 M HCl (1 h; 80° C.), followed by quantitative analysis of the released sialic acids by HPAEC-PAD, yielded a sialic acid content of 1.4%, built up from 72% Neu5Ac and 28% Neu5Gc.

From the literature it is known that the O-glycans of PSMG contain an array of oligosaccharides with both ($\alpha$2-3)- and/or ($\alpha$2-6)-linked sialic acid (Hansson et al., Carbohydr. Res. 221: 179-189, 1991). Of these two linkage positions, only the ($\alpha$2-3)-linked sialic acid acts as an effective donor for TcTS. TcTS (2-8 mU/ml) incubations with PSMG (0.5 mM total Neu5Ac, ($\alpha$2-3)- and ($\alpha$2-6)-linked) and 10 mM lactose resulted after 24 h in the transfer of up to 10% of the total Neu5Ac into 3'NeuSAc-lactose (HPAEC-PAD). Similar levels of Neu5Gc were transferred to lactose, yielding 3'NeuSGc-lactose. When using partially purified PSMG, obtained via Sepharose CL-4B chromatography and concentrated on a spin-filter with a cut-off value of 50 kDa, or ethanol-precipitated PSMG, the transfer of total Neu5Ac to lactose could be increased to about 20% and of total Neu5Gc to about 15%. Taking into account the linkage specificity, the actual conversion efficiency of ($\alpha$2-3)-linked Neu5Ac into 3'SL (Neu5Ac) is 45%.

Example 7

Production of Sia-GOS (Sia=Neu5Ac) at the Gram Scale Using GMP as Donor, Vivinal-GOS as Acceptor, and TcTS as a Biocatalyst

*E. coli* TOP10 cells harboring pTrcTS611/2 were inoculated in terrific broth medium (50 ml), containing 0.1 mM IPTG and 100 µg/ml ampicillin, and cultured for 20 h at 30° C. on a rotary shaker. The cells were harvested by centrifugation and chemically lysed using bacterial protein extraction reagent (B-PER, Thermo scientific). The TcTS protein was purified using His-tagged immobilized metal affinity chromatography (eluent, 100 mM imidazole). The purified protein fractions obtained from 10 different 50-ml cultures were pooled and, to remove imidazole, subsequently washed and concentrated using an Amicon 50 kDa spinfilter. The washed protein was eventually buffered in 50 mM Tris-HCl (pH 8) containing 15% glycerol.

To determine the optimal sialic acid transfer in time, in test experiments TcTS was added (final conc. of 2 mU/ml) to various concentrations of GMP-bound Neu5Ac (donor; a commercial GMP product (sialic acid content: 4.0%; containing 10% (w/w) NaCl) and lactose (acceptor). An excess of donor substrate led to high conversion of the acceptor. Incubations for more than 48 h under the conditions tested led to hydrolysis (a side reaction of the TcTS enzyme) of the product. Typically, a mM ratio of Neu5Ac:lactose=5:1 yielded 82% 3'SL (Neu5Ac) after 24 h, 100% after 48 h, and 76% after 70 h; and a mM ratio of Neu5Ac:lactose=5:2 gave 56% 3'SL (Neu5Ac) after 24 h, 75% after 48 h, and 61% after 70 h.

An 800-ml reaction mixture, containing 5 mM ($\alpha$2-3)-linked Neu5Ac (~46 g/l GMP), 2 mM GOS (Vivinal-GOS) and 2 mU/ml TcTS in 50 mM Na-citrate (pH 5), was incubated for 48 at 25° C. Before use, crude GMP, containing relatively high amounts of NaCl, was desalted via a polyethersulfone membrane filter with a 3 kDa cut-off value.

After a heat inactivation step (20 min at 60° C.), partially desialylated and starting GMP were removed via a filtration step (3 kDa membrane filter). Qualitative analysis of the total permeate before and after mild acid hydrolysis (release of Neu5Ac), using the AOAC method (employing $\beta$-galactosidase from *Aspergillus oryzae*) to quantitatively measure GOS contents, showed that 48% non-sialylated GOS was present and 52% sialylated GOS. The total permeate was lyophilized and desalted by gel-filtration on Bio-Gel P-2 using demiwater as eluent. As checked by HPAEC-PAD, the first eluting fractions contained the mixture of mono-Sia-GOS and di-Sia-GOS (Sia=Neu5Ac), essentially free of NaCl, followed by free Neu5Ac and decreasing DPs of non-sialylated GOS. MALDI-TOF-MS analysis showed sialylated GOS products obtained from GOS up to GOS DP7.

Example 8

TcTS-Catalyzed Incubation of Vivinal GOS DP3 and GMP

A TcTS (2.5 mU/ml) catalyzed incubation of GOS DP3 (3 mM) with GMP (sialic acid content: 4.0%; 6 mM ($\alpha$2-3)-linked Neu5Ac) was carried out for 23 h at 25° C. and pH 5. After work-up, the oligosaccharide product was subjected to anion-exchange chromatography on Resource Q, with detection at 214 nm, yielding a mono-Sia-GOS DP3 and a di-Sia-GOS DP3 fraction in a molar ratio of 88:12. Verifications were carried out by MALDI-TOF-MS and $^1$H NMR spectroscopy. Further analysis of the di-Sia-GOS DP3 fraction with a focus on "branched reducing" and "non-branched non-reducing" forms, making use of a $NaBH_4$ reduction step followed by HPAEC-PAD and MALDI-TOF-MS, showed that the major part of di-Sia-GOS DP3 consists of branched structures.

Example 9

TcTS-Catalyzed incubation of Vivinal GOS DP4 and GMP

A TcTS (2.5 mU/ml) catalyzed incubation of GOS DP4 (3 mM) with GMP (sialic acid content: 4.0%; 6 mM ($\alpha$2-3)-linked Neu5Ac) was carried out for 23 h at 25° C. and pH 5. After work-up, the oligosaccharide product was subjected to anion-exchange chromatography on Resource Q, with detection at 214 nm, yielding a mono-Sia-GOS DP4 and a di-Sia-GOS DP4 fraction in a molar ratio of 91:9. Verifications were carried out by MALDI-TOF-MS and $^1$H NMR spectroscopy. Further analysis of the di-Sia-GOS DP4 fraction with a focus on "branched reducing" and "non-branched non-reducing" forms, making use of a $NaBH_4$ reduction step followed by HPAEC-PAD and MALDI-TOF-MS, showed that the major part of di-Sia-GOS DP4 consists of branched structures.

Example 10

TcTS-Catalyzed Incubation of Vivinal GOS DP5 and GMP

A TcTS (2.5 mU/ml) catalyzed incubation of GOS DP5 (3 mM) with GMP (sialic acid content: 4.0%; 6 mM ($\alpha$2-3)-linked Neu5Ac) was carried out for 23 h at 25° C. and pH 5. After work-up, the oligosaccharide product was subjected to anion-exchange chromatography on Resource Q, with detection at 214 nm, yielding a mono-Sia-GOS DP5 and a di-Sia-GOS DP5 fraction in a molar ratio of 88:12. Verifications were carried out by MALDI-TOF-MS and $^1$H NMR spectroscopy. Further analysis of the di-Sia-GOS DP5 fraction with a focus on "branched reducing" and "non-branched non-reducing" forms, making use of a NaBH$_4$ reduction step followed by HPAEC-PAD and MALDI-TOF-MS, showed that the major part of di-Sia-GOS DP5 consists of branched structures.

Example 11

TcTS-Catalyzed Incubation of Vivinal GOS DP6-8 and GMP

Individual incubations of Vivinal GOS DP6, DP7 and DP8 with TcTS and GMP, according to the protocol described in examples 8-10 yielded a mono-Sia-GOS DP6 and a di-Sia-GOS DP6 fraction in a molar ratio of 87:13, a mono-Sia-GOS DP7 and a di-Sia-GOS DP7 fraction in a molar ratio of 84:16, and a mono-Sia-GOS DP8 and a di-Sia-GOS DP8 fraction in a molar ratio of 81:19.

Example 12

TcTS-Catalyzed Incubation of Vivinal GOS DP3 and DP4 and PSMG

A TcTS (3 mU/ml) catalyzed incubation of GOS DP3 (3 mM) or GOS DP4 (3 mM) with ethanol-precipitated PSMG (2 mM) was carried out for 23 h at 25° C. and pH 5. After work-up, the oligosaccharide products were subjected to MALDI-TOF-MS analysis showing in each case Neu5Ac and Neu5Gc sialylation.

Example 13

Nutritional Formulas for Infants

Table 2 shows the composition (per 100 ml) of three exemplary nutritional formulas according to the invention, e.g. infant formulas for the age group between 0-6 months, for supporting or enhancing the infant's immune system.

Example 14

Animal Feed Formula

The animal feed is composed of a basic feed, supplemented with amongst others a disialo ingredient.

| Basic feed | |
|---|---|
| Barley | 27.45% |
| Maize | 20.00% |
| Wheat | 24.84% |
| Soya meal, high protein | 4.82% |
| Sunflower seed, extracted | 2.00% |
| Whey powder | 7.44% |
| Molasses | 1.00% |
| Feed fats | 1.04% |
| Soya oil | 0.50% |
| Premix | 0.50% |
| Calcium carbonate | 1.08% |
| Mono calcium phosphate | 0.19% |

| Feed for Young piglets High level of sialic acid in ingredient | |
|---|---|
| Basic feed | 91.52% |
| Potato protein | 0.50% |
| Whey powder | 4.37% |
| Soycomill P | 0.50% |
| Disialo ingredient | 3.00% |

| Feed for young piglets Low level of sialic acid in ingredient | |
|---|---|
| Basic feed | 91.52% |
| Potato protein | 0.50% |
| Whey powder | 6.37% |
| Soycomill P | 0.50% |
| Disialo ingredient | 1.00% |

TABLE 2 composition of the formulas (per 100 ml)

| | Basic | Formula A: disialo ingredient | Formula B: disialo ingredient + sialyllactose | Formula C: disialo ingredient + sialyllactose + GOS | Formula D: disialo ingredient + sialyllactose + GOS + fucosyllactose |
|---|---|---|---|---|---|
| Energy, kcal | 67 | 67 | 67 | 67 | 67 |
| Protein (g) | 1.4 | 1.4 | 1.4 | 1.4 | 1.4 |
| Carbohydrates (g) | 7.6 | 7.4 | 7.4 | 6.7 | 6.7 |
| Fat (g) | 3.5 | 3.5 | 3.5 | 3.5 | 3.5 |
| Disialo ingredient (g) | | 0.25 | 0.13 | 0.1 | 0.1 |
| Sialyllactose (g) | | | 0.13 | 0.1 | 0.1 |
| Vivinal GOS (g) | | | | 0.5 | 0.4 |
| Fucosyllactose (g) | | | | | 0.1 |

| Feed for young piglets Lower level of sialic acid in ingredient | |
|---|---|
| Basic feed | 91.52% |
| Potato protein | 0.50% |
| Whey powder | 6.98% |
| Soycomill P | 0.50% |
| Disialo ingredient | 0.50% |

| Feed for young piglets Lowest level of sialic acid in ingredient | |
|---|---|
| Basic feed | 91.52% |
| Potato protein | 0.50% |
| Whey powder | 7.38% |
| Soycomill P | 0.50% |
| Disialo ingredient | 0.10% |

| Feed for young piglets In combination with blood plasma | |
|---|---|
| Basic feed | 91.52% |
| Potato protein | 0.50% |
| Whey powder | 5.88% |
| Soycomill P | 0.50% |
| Disialo ingredient | 0.10% |
| Blood plasma | 1.50% |

Example 15

Effect of Di-Sia-GOS Enriched Fraction on In Vivo Pathogen Adhesion

A neonatal rat model of necrotizing enterocolitis (NEC) can be used to objectively evaluate the protective effects of a di-Sia-GOS-enriched fraction by the clinical behaviour of the animals and the macroscopic appearance of the gut.

Materials and Methods: Neonatal rats are delivered at term and assigned either to a control group (A) consisting of breastfeeding and no stress factors, to a NEC group (B) in which NEC is induced by gavage feeding+hypoxia+oral lipopolysaccharide (4 mg/kg/day once daily for the first 2 days of life), or to a treated NEC group (C) in which NEC is induced by gavage feeding+hypoxia+oral lipopolysaccharide (4 mg/kg/day once daily for the first 2 days of life) plus di-Sia-GOS. Clinical status is assessed on day 4 using a clinical sickness score (general appearance, response to touch, natural activity, body Colour; 0-3 for each variable). Neonatal rats are sacrificed at 4 different time points: day 1, day 2, day 3, and day 4. At sacrifice, a macroscopic assessment of the gut is performed using a scoring system based on: colour (0-2), consistency (0-2) and degree of dilatation (0-2). The resected gut is stained with haematoxylin/eosin, and evaluated microscopically by 2 independent blinded scorers, including a consultant histopathologist. The histology results can be used to validate the macroscopic gut assessment. Results are compared by ANOVA and linear regression analysis.

REFERENCES

R. Agusti, M. E. Giorgi, and R. M. de Lederkremer, The trans-sialidase from *Trypanosoma cruzi* efficiently transfers ($\alpha2 \rightarrow 3$)-linked N-glycolylneuraminic acid to terminal β-galactosyl units. Carbohydr. Res. 342 (2007) 2465-2469.

S. Asakuma, M. Akahori, K. Kimura, Y. Watanabe, T. Nakamura, M. Tsunemi, I. Arai, Y. Sanai, and T. Urashima, Sialyl oligosaccharides of human colostrum: Changes in concentration during the first three days of lactation, Biosc. Biotechnol. Biochem. 71 (2007) 1447-1451.

L. Coulier, J. Timmermans, R. Bas, R. van den Dool, I. Haaksman, B. Klarenbeek, T. Slaghek, and W. van Dongen, In-depth characterization of prebiotic galacto-oligosaccharides by a combination of analytical techniques, J. Agr. Food Chem. 57 (2009) 8488-8495.

C. T. M. Fransen, Structural analysis of soy bean polysaccharides and transgalactosylation products from lactose, PhD thesis Utrecht University (1999).

C. T. M. Fransen, K. M. J. Van Laere, A. A. C. van Wijk, L. P. Brüll, M. Dignum, J. E. Thomas-Oates, J. Haverkamp, H. A. Schols, A. G. J. Voragen, J. P. Kamerling, and J. F. G. Vliegenthart, α-D-Glcp-($1 \leftrightarrows 1$)-β-D-Galp-containing oligosaccharides, novel products from lactose by the action of β-galactosidase, Carbohydr. Res. 314 (1998) 101-114.

A. K. Goulas, P. G. Kapasakalidis, H. R. Sinclair, R. A. Rastall, and A. S. Grandison, Purification of oligosaccharides by nanofiltration, J. Membr. Sc. 209 (2002) 321-335.

G. C. Hansson, J.-F. Bouhours, H. Karlsson, and I. Carlstedt, Analysis of sialic acid-containing mucin oligosaccharides from porcine small intestine by high-temperature gas chromatography-mass spectrometry of their dimethylamides, Carbohydr. Res. 221 (1991) 179-189.

T. Idota, H. Kawakami, Y. Murakami, and M. Sugawara, Inhibition of cholera toxin by human milk fractions and sialyllactose, Biosci. Biotech. Biochem. 59 (1995) 417-419.

B. Neubacher, D. Schmidt, P. Ziegelmuller, and J. Thiem, Preparation of sialylated oligosaccharides employing recombinant trans-sialidase from *Trypanosoma cruzi*. Org. Biomol. Chem. 3 (2005) 1551-1556.

G. Paris, M. L. Cremona, M. F. Amaya, A. Buschiazzo, S. Giambiagi, A. C. C. Frasch, and P. M. Alzari, Probing molecular function of trypanosomal sialidases: single point mutations can change substrate specificity and increase hydrolytic activity, Glycobiology 11 (2001) 305-311.

R. Schauer and J. P. Kamerling, The chemistry and biology of Trypanosomal trans-sialidases: virulence factors in Chagas disease and sleeping sickness, ChemBioChem 12 (2011) 2246-2264.

P. Scudder, J. P. Doom, M. Chuenkova, I. D. Manger, and M. E. A. Pereira, Enzymatic characterization of β-D-galactoside α-2,3-trans-sialidase from *Trypanosoma cruzi*, J. Biol. Chem. 268 (1993) 9886-9891.

P. M. Simon, P. L. Goode, A. Mobasseri, and D. Zopf, Inhibition of *Helicobacter pylori* binding to gastrointestinal epithelial cells by sialic acid-containing oligosaccharides, Infection and Immunity 65 (1997) 750-757.

S. Thurl, M. Munzert, J. Henker, G. Boehm, B. Müller-Werner, J. Jelinek, and B. Stahl, Variation of human milk oligosaccharides in relation to milk groups and lactational periods, British J. Nutr. 104 (2010) 1261-1271.

W. B. Turnbull, J. A. Harrison, K. P. Ravindranathan Kartha, S. Schenkman, and R. A. Field, Observations on chemical and enzymatic approaches to α-2,3-sialylated octyl β-lactoside, Tetrahedron 58 (2002) 3207-3216.

H. van Halbeek, L. Dorland, J. F. G. Vliegenthart, A.-M. Fiat, and P. Jones, A 360-MHz $^1$H-NMR study of three oligosaccharides isolated from cow ic-casein, Biochim. Biophys. Acta 623 (1980) 295-300.

S. Yanahira, T. Kobayashi, T. Suguri, M. Nakakoshi, S. Miura, H. Ishikawa, and I. Nakajima, Formation of oligosaccharides from lactose by *Bacillus circulans* β-galactosidase, Biosc. Biotech. Biochem. 59 (1995) 1021-1026.

The invention claimed is:

1. A method for providing a composition comprising sialic acid containing oligosaccharides, comprising the steps of:
   a) providing a source of non-digestible galactooligosaccharides (GOS) containing at least two terminally bonded β-linked galactose residues;
   b) providing a sialic acid donor having (α2-3)-sialylated O-glycans;
   c) contacting said GOS with said sialic acid donor in the presence of an enzyme having trans-sialidase activity in an enzyme reaction mixture; and
   d) obtaining from said enzyme reaction mixture a fraction comprising at least 5 percent by weight of disialylated galactooligosaccharides (di-Sia-GOS) based on the dry matter.

2. Method according to claim 1, wherein said source of galactooligosaccharide is the product obtained by enzymatic treatment of lactose or a mixture of lactose and trehalose with β-galactosidase (EC 3.2.1.23).

3. Method according to claim 1 wherein said di-Sia-GOS have a degree of polymerization (DP) within the range of DP4 to DP10.

4. Method according to claim 1, wherein said sialic acid donor is a naturally occurring compound selected from sialic acids bonded to oligosaccharides, polysaccharides, polysialic acids, glycoproteins and glycolipids.

5. Method according to claim 4, wherein said sialic acid donor is selected from the group consisting of glycosylated whey proteins and casein, and fragments of the same.

6. Method according to claim 4, wherein said sialic acid donor is selected from the group consisting of glycosylated mucus proteins, and fragments of the same.

7. Method according to claim 6, wherein said sialic acid donor is the product obtained from mucin, optionally followed by concentration of Sia-containing mucin polymers.

8. Method according to claim 1, wherein said enzyme having trans-sialidase activity is encoded by a gene product from microorganisms of the *Trypanosoma* genus, preferably *Trypanosoma cruzi* or *Trypanosoma* congolense.

9. Method according to claim 1, wherein said enzyme is recombinantly produced.

10. Method according to claim 1, wherein the pH of the enzyme reaction mixture ranges between 4 and 6.

11. Method according to claim 1, wherein step d) comprises a separation technique based on a difference in charge between components to be separated.

12. Method according to claim 1, wherein step d) comprises a separation technique based on a difference in size between components to be separated.

13. A method for providing an infant formula, comprising
   a) providing a source of non-digestible galactooligosaccharides (GOS) containing at least two terminally bonded β-linked galactose residues;
   b) providing a sialic acid donor having (α2-3)-sialylated O-glycans;
   c) contacting said GOS with said sialic acid donor in the presence of an enzyme having trans-sialidase activity in an enzyme reaction mixture; and
   d) obtaining from said enzyme reaction mixture a fraction comprising at least 5 percent by weight of disialylated galactooligosaccharides (di-Sia-GOS) based on the dry matter, and
   e) formulating said fraction into an infant formula together with a protein source, a fat source and a carbohydrate source.

14. Method according to claim 3 wherein said di-Sia-GOS have a degree of polymerization (DP) within the range of DP5 to DP8.

15. Method according to claim 5, wherein said sialic acid donor is glycomacropeptide from κ-casein (GMP).

16. Method according to claim 6, wherein said sialic acid donor is pig small intestinal glycoprotein (PSMG).

17. Method according to claim 10, wherein the pH of the enzyme reaction mixture ranges between 4.8 and 5.8.

18. Method according to claim 11, wherein step d) comprises anion exchange chromatography.

19. Method according to claim 12, wherein step d) comprises size-exclusion chromatography.

* * * * *